United States Patent [19]

Imai

[11] 4,435,607

[45] Mar. 6, 1984

[54] DEHYDROGENATION OF DEHYDROGENATABLE HYDROCARBONS

[75] Inventor: Tamotsu Imai, Mount Prospect, Ill.

[73] Assignee: UOP Inc., Des Plaines, Ill.

[21] Appl. No.: 421,628

[22] Filed: Sep. 22, 1982

Related U.S. Application Data

[63] Continuation-in-part of Ser. No. 258,358, Apr. 28, 1981, abandoned.

[51] Int. Cl.$^3$ .......................... C07C 5/40; C07C 5/48
[52] U.S. Cl. .................................. 585/443; 585/319; 585/440; 585/444; 585/654; 585/659; 585/660
[58] Field of Search ............... 585/319, 440, 443, 444, 585/654, 659, 660, 441

[56] References Cited

U.S. PATENT DOCUMENTS

| | | | |
|---|---|---|---|
| 3,417,156 | 12/1968 | Berger | 585/441 |
| 3,515,763 | 6/1970 | Uitti | 585/441 |
| 3,670,044 | 6/1972 | Drehman et al. | 585/443 |
| 3,742,078 | 6/1973 | Hayes | 585/444 |
| 3,755,481 | 8/1973 | Hayes | 585/444 |
| 3,755,486 | 8/1973 | Wilhelm | 585/444 |
| 3,855,330 | 12/1974 | Mendelsohn et al. | 585/443 |
| 3,856,870 | 12/1974 | Hayes | 585/443 |
| 3,904,703 | 9/1975 | Lo et al. | 585/441 |
| 4,177,218 | 12/1979 | Antos | 585/443 |

*Primary Examiner*—Delbert E. Gantz
*Assistant Examiner*—A. Pal
*Attorney, Agent, or Firm*—James R. Hoatson, Jr.; Raymond H. Nelson; William H. Page, II

[57] ABSTRACT

Dehydrogenatable hydrocarbons may be subjected to a dehydrogenation reaction in which the hydrocarbons are treated with a dehydrogenation catalyst such as a modified iron compound in the presence of steam in a multi-catalyst bed system. The reaction mixture containing unconverted hydrocarbon, dehydrogenated hydrocarbon, hydrogen and steam is then contacted with a selective oxidation catalyst such as a noble metal of Group VIII of the Periodic Table, a metal of Group IVA of the Periodic Table and, if so desired, a metal of Group IA or IIA of the Periodic Table composited on a highly porous inorganic support. The oxidation catalyst will selectively oxidize the hydrogen to improve the combustion thereof and supply the necessary heat required for a subsequent dehydrogenation treatment.

11 Claims, No Drawings

DEHYDROGENATION OF DEHYDROGENATABLE HYDROCARBONS

CROSS-REFERENCE TO RELATED APPLICATIONS

This application is a continuation-in-part of my copending application Ser. No. 258,358 filed Apr. 28, 1981, and now abandoned all teachings of which are incorporated herein by reference thereto.

BACKGROUND OF THE INVENTION

It has been known in the prior art that unsaturated hydrocarbons may be obtained from the dehydrogenation of dehydrogenatable hydrocarbons. The dehydrogenation may be effected by subjecting the dehydrogentable hydrocarbons to a dehydrogenation process at dehydrogenation conditions in the presence of certain catalytic compositions of matter which possess the ability to dehydrogenate said compounds with the resultant formation of olefinic hydrocarbons. The particular dehydrogenation catalysts which are employed are well known in the art and comprise such compounds as nickel composited on a solid support such as diatomaceous earth, kieselguhr, charcoal and iron composited on the same supports, etc.

Other dehydrogenation processes have employed, in addition to the dehydrogenation catalysts, an oxidation catalyst in the reaction process. The presence of the oxidation catalyst is necessitated by the fact that it is advantageous to oxidize the hydrogen which is produced by contact with an oxygen-containing gas in order to maintain the desired reaction temperature. For example, styrene, which is an important chemical compound utilized for the preparation of polystyrene, plastics, resins or synthetic elastomers such as styrene-butadiene rubber, etc., may be prepared from the dehydrogenation of ethylbenzene. The dehydrogenation of ethylbenzene into styrene, which is effected by treating ethylbenzene with steam in the presence of a modified iron catalyst, is endothermic in nature. The heat of reaction is about 30 Kcal per mole of ethylbenzene. Therefore, the temperature of the catalyst bed decreases significantly during the progress of the reaction in a commercial adiabatic reactor resulting in limitation of ethylbenzene conversion to a low level. The limitation of conversion arises from the fact that the equilibrium conversion of ethylbenzene is lowered and the rate of ethylbenzene dehydrogenation decreases as the reaction temperature decreases. The decrease of temperature adversely affects not only the conversion level, but also the selectivity for styrene, since at equilibrium conditions, only undesirable side reactions continue to take place. Therefore, it is necessary to maintain the desired temperature level in order to provide a high equilibrium conversion level and a high reaction rate. In the conventional process, the maintenance of temperature is attained by reheating the product stream with the addition of superheated steam between dehydrogenation catalyst beds using a multi-catalyst bed reactor system. However, consumption of the additional superheated steam is considerably high and makes the dehydrogenation process costly. Accordingly, significant process economic improvements over the conventional ethylbenzene dehydrogenation processes can be achieved if the reaction temperature is somehow maintained while eliminating or reducing the additional superheated steam. One method of providing for the maintenance of the reaction temperature is to introduce oxygen into the reaction mixture by way of oxygen or an oxygen-containing gas such as air which will burn the hydrogen formed during the dehydrogenation reaction, this combustion resulting in an exothermic reaction which will provide the necessary amount of heat and, in addition, will shift the equilibrium toward production of styrene since the hydrogen formed in the dehydrogenation is consumed. Consequently, a higher conversion and higher styrene selectivity are achievable.

The combustion of hydrogen with the oxygen in the oxygen-containing gas requires the presence of an oxidation catalyst. There are some key requirements for the oxidation catalyst to be usable for such a purpose. The most important catalytic property required is good catalytic stability since the oxidation catalyst must survive under very severe reaction conditions, namely at about 600° to 650° C. in the presence of steam. Under such conditions, porous inorganic materials such as aluminas, silicas and zeolites cannot maintain their pore structures for a long period of time, resulting in the permanent damage of catalysts prepared using such materials as supports, e.g. platinum supported on a porous high surface area alumina, silica, or zeolite. Secondly, the oxidation catalyst must be very active to achieve complete conversion of oxygen to avoid poisoning of iron-based dehydrogenation catalysts which are sensitively oxidized with oxygen to lose their dehydrogenation activities. Thirdly, the oxidation catalyst must be selective for oxidation of hydrogen. Otherwise, ethylbenzene and styrene are consumed to lower the efficiency of styrene production.

Various U.S. patents have described types of oxidation catalysts which may be employed in this process. For example, U.S. Pat. No. 3,437,703 describes a catalytic dehydrogenation process which employs, as a dehydrogenation catalyst, a composition known in the trade as Shell-105 which consists of from 87% to 90% ferric oxide, 2% to 3% chromium oxide, and from 8% to 10% of potassium oxide. In addition, another dehydrogenation catalyst which is employed comprises a mixture of nickel, calcium, chromic oxide, graphite with a major portion of a phosphate radical. In addition to these dehydrogenation catalysts, the reaction also employs a catalyst for the oxidation step of the process comprising platinum or palladium in elemental form or as a soluble salt. Another U.S. Pat. No. namely 3,380,931, also discloses an oxidation catalyst which may be used in the oxidative dehydrogenation of compounds such as ethylbenzene to form styrene comprising an oxide of bismuth and an oxide of a metal of Group VIB of the Periodic Table such as molybdenum oxide, tungsten oxide or chromium oxide. In addition, the patent also states that minor amounts of arsenic may also be present in the catalytic composite as well as other metals or metalloids such as lead, silver, tin, manganese, phosphorus, silicon, boron and sulfur.

U.S. Pat. No. 3,855,330 discloses a method for the production of styrene in which ethylbenzene is treated in the vapor state of passage over a dehydrogenation catalyst and an oxidation catalyst while introducing oxygen into the reaction medium. The dehydrogenation catalysts which are employed are those which have been set forth in various prior U.S. patents and which may be similar in nature to the dehydrogenation catalysts previously discussed. The types of oxidation catalysts which may be employed will include platinum or palladium catalysts which are composited on alumina or molecular screens of the zeolite type which have been charged with ferrous, heavy or noble metals. The patent lists the types of catalysts which are employed including copper or various zeolites, platinum on alumina, platinum on spinel, platinum and sodium on zeolites, platinum, sodium and potassium on zeolites, etc.

U.S. Pat. No. 3,670,044 discloses a method for dehydrogenating cycloalkane, arylalkane and alkanes in the presence of gaseous hydrogen or mixture of gaseous hydrogen and gaseous oxygen using a catalyst composition comprising a Group VIII metal or a mixture of a Group VIII metal and a Group IVA metal deposited on a support comprising a Group II aluminate spinel. It is noted that the patentee teaches that added hydrogen is used in connection with the oxygen, and that when only oxygen is used, the conversion and selectivity are generally low. The addition of hydrogen is believed to be a significant disadvantage in the dehydrogenation process inasmuch as the equilibrium conversion is lowered. This is in contradistinction to the process of the present invention wherein the dehydrogenation process, prior to the oxidation step, is not effected in the presence of any added hydrogen. As will hereinafter be shown in greater detail, the present process results in the selective oxidation of hydrogen with a concomitantly lower selectivity to carbon monoxide and carbon dioxide. In addition, the patentee teaches the use of one catalyst for both dehydrogenation and oxidation which is in contrast to the separate dehydrogenation and oxidation catalysts which are used in the present process.

In a process for the dehydrogenation of dehydrogentable hydrocarbons wherein said hydrocarbons are treated with steam and a dehydrogenation catalyst along with a subsequent or concurrent treatment with an oxygen-containing gas in the presence of an oxidation catalyst, it will hereinafter be shown that by utilizing a catalyst of the type of the present invention, it is possible to obtain the desired product in an excellent yield with a concomitant use of the catalyst for a longer period of time due to the excellent stability of the catalyst during the reaction period.

BRIEF SUMMARY OF THE INVENTION

This invention relates to a process for the dehydrogenation of dehydrogenatable hydrocarbons. More specifically, the invention is concerned with a process for the dehydrogenation of dehydrogenatable hydrocarbons in which the hydrocarbon is subjected to a dehydrogenation step in the presence of a dehydrogenation catalyst followed by a selective oxidation step in which the product mixture from the dehydrogenation step is treated in the presence of certain catalytic compositions of matter hereinafter set forth in greater detail whereby the hydrogen which is present from the dehydrogenation step is selectively oxidized with a minimum oxidation of the hydrocarbons. By utilizing the particular selective oxidation catalyst, it is possible to obtain dehydrogenated hydrocarbons in a relatively high yield as well as maintaining the stability and activity of the catalyst, thereby obviating the necessity for regenerating or changing the catalyst, and thus adding to the economic feasibility of the dehydrogenation process.

It is therefore an object of this invention to provide a process for the dehydrogenation of dehydrogenatable hydrocarbons.

A further object of this invention is to provide a dehydrogenation process utilizing, in one step of the process, a selective oxidation catalyst.

In one aspect, an embodiment of this invention resides in a process for the dehydrogenation of a dehydrogenatable hydrocarbon which comprises contacting said hydrocarbon with a dehydrogenated catalyst comprising an alkaline metal-promoting iron compound at dehydrogenation conditions in the presence of steam in a first dehydrogenation zone, and thereafter contacting the resultant mixture of unconverted hydrocarbons, dehydrogenated hydrocarbons, hydrogen and steam with an oxygen-containing gas in the presence of an oxidation catalyst comprising a noble metal of Group VIII and a metal of Group IVA of the Periodic Table composited on a highly porous inorganic support at oxidation conditions in an oxidation zone and selectively oxidizing hydrogen contained in said mixture to reheat said mixture to dehydrogenation temperature by internal catalytic combustion of the hydrogen, contacting the thus reheated mixture with additional dehydrogenation catalyst comprising an alkaline metal-promoting iron compound at dehydrogenation conditions in a first dehydrogenation zone, and recovering the dehydrogenated hydrocarbon.

A specific embodiment of this invention is found in a process for the dehydrogenation of ethylbenzene which comprises contacting said ethylbenzene with a dehydrogenation catalyst comprising a modified iron catalyst at a temperature in the range of from about 500° to about 700° C. and a pressure in the range of from about 0.1 to about 10 atmospheres in the presence of steam, thereafter contacting the resultant mixture of unconverted ethylbenzene, styrene, hydrogen and steam with air in the presence of a catalyst comprising a mixture of platinum, tin, and potassium composited on alumina at a temperature in the range of from about 500° to about 700° C. and a pressure in the range of from about 0.1 to about 10 atmospheres whereby hydrogen is selectively oxidized, and recovering styrene.

Other objects and embodiments will be found in the following further detailed description of the present invention.

DETAILED DESCRIPTION OF THE INVENTION

As hereinbefore set forth, the present invention is concerned with a hydrogenation process which involves the use, in one step of the process, of a selective oxidation catalyst. In the present process, a dehydrogenatable hydrocarbon of the type hereinafter set forth in greater detail, is contacted with a dehydrogenation catalyst in the presence of steam in a multi-catalyst bed system. Inasmuch as the dehydrogenation of the hydrocarbon is endothermic in nature, it is necessary to provide an additional amount of heat before the product enters the next catalyst bed, the reaction temperature being held at a relatively high rate in order to provide a high equilibrium conversion as well as a high reaction rate. One method of effecting this increase in the desired temperature is to provide an internal catalytic combustion of the hydrogen which is produced during the dehydrogenation reaction in order to reheat the product to the desired level. By effecting a selective oxidation of the hydrogen, it is possible to avoid the use of superheated steam or other outside sources of heat. This selective oxidation of hydrogen with the resultant composition thereof is effected by utilizing a selective oxidation catalyst of the type hereinafter set forth in greater detail, the selective oxidation catalyst maintaining its stability and activity for a considerable length of time.

The process of the present invention may be effected by utilizing an apparatus in which the dehydrogenation catalyst and the oxidative catalyst, both of the type hereinafter set forth in greater detail, are loaded in the apparatus in alternate layers. The number of alternate layers of dehydrogenation catalyst and selective oxidative catalyst may vary according to the size or type of apparatus which is employed, the number of alternate layers ranging from three to about nine. As will hereinafter be shown, the dehydrogenation catalyst and the oxidation catalyst are different in nature. Examples of dehydrogenation catalysts which may be employed will comprise an alkaline earth metal-promoted iron compound. The term "alkaline metal" as used in the present specification and appended claims will refer to metals of Groups IA and IIA of the Periodic Table which includes lithium, sodium, potassium, rubidium, cesium, beryllium, magnesium, calcium, strontium and barium. In addition, the promoted iron compound catalyst will, in the preferred embodiment of the invention, also include a compound containing a metal of Groups IVB, VB and VIB of the Periodic Table. For example, a typical dehydrogenation catalyst which may be employed in the process of this invention will consist essentially of about 85% by weight of ferric oxide, 12% by weight of potassium hydroxide, 2% by weight of chromia and 1% by weight of sodium hydroxide. Another typical dehydrogenation catalyst which may be used comprises 90% by weight of ferric oxide, 4% by weight of chromia and 6% by weight of potassium carbonate. In addition to these catalysts, other well-known dehydrogenation catalysts which may be utilized will include those comprising ferric oxide, potassium oxide, as well as other metal oxides and/or sulfides of metals of Groups IA, IIA, IVB, VB and VIB of the Periodic Table including those of calcium, lithium, strontium, magnesium, beryllium, zirconium, tungsten, molybdenum, hafnium, vanadium, copper, chromium and mixture of two or more oxides such as chromia-alumina, chromiatitania, alumina-vanadia and the like.

The dehydrogenation of a dehydrogenatable hydrocarbon such as, for example, ethylbenzene, is effected by contacting the dehydrogenatable hydrocarbon and steam, in the absence of any added hydrogen, with the aforesaid catalyst at dehydrogenation conditions which are in the range of from about 500° to about 700° C. and at a reaction pressure in the range of from about 0.1 to about 10 atmospheres; the exact dehydrogenation conditions are, however, a function of the particular dehydrogenatable hydrocarbon undergoing dehydrogenation. Other reaction conditions will include a Liquid Hourly Space Velocity based on the hydrocarbon charge of from about 0.1 to about 10 hrs$^{-1}$ and steam to hydrocarbon weight ratios ranging from about 1:1 to about 40:1. The number of dehydrogenation zones of the catalyst beds may vary from 1 to about 5 in number and typically may comprise three reaction zones; however, the number of zones is not critical to the invention. After contacting the dehydrogenation catalyst with the steam and hydrocarbon the resulting mixture comprising unconverted hydrocarbon, dehydrogenated hydrocarbon, steam and hydrogen which has passed through the catalyst bed is contacted in a separate zone with the selective oxidative catalytic composition of the type hereinafter set forth in greater detail. In addition, oxygen-containing gas is introduced into the reactor, preferably at a point adjacent to the oxidative catalyst bed. Examples of oxygen-containing bases which may be utilized to effect the selective oxidation of the hydrogen which is present will include air, oxygen, air or oxygen diluted with other gases such as steam, carbon dioxide and inert gases such as nitrogen, argon, helium, etc. The amount of oxygen which is introduced to contact the product stream may range from about 0.1:1 to about 2:1 moles of oxygen per mole of hydrogen contained in the product stream. In this particular reaction zone, the product stream, which comprises unreacted dehydrogenatable hydrocarbon, dehydrogenated hydrocarbon, hydrogen and steam, undergoes a selective oxidation in contact with oxygen and the oxidative catalyst whereby hydrogen is selectively oxidized to water with a minimal amount of reaction of oxygen with the hydrocarbons, either unconverted hydrocarbon or dehydrogenated hydrocarbon.

After passage through the zone containing the oxidation catalyst, the mixture may then be passed through a second dehydrogenation zone containing a dehydrogenation catalyst of the type hereinbefore set forth for further dehydrogenation, the process being completed through the plurality of zones followed by withdrawal of the product stream and separation of the unconverted hydrocarbon from the desired dehydrogenated product.

It is contemplated that the dehydrogenation process for the dehydrogenation of dehydrogenatable hydrocarbons utilizing the oxidative catalytic compositions of matter of the present invention will be applicable to a wide variety of dehydrogenatable hydrocarbons. Examples of hydrocarbons which are susceptible to a dehydrogenation process utilizing the catalysts of the present invention will include lower alkyl-substituted aromatic hydrocarbons such as ethylbenzene, diethylbenzene, isopropylbenzene, diisopropylbenzene, o-ethyltoluene, m-ethyltoluene, p-ethyltoluene, o-isopropyltoluene, m-isopropyltoluene, p-isopropyltoluene, ethylnaphthalene, propylnaphthalene, isopropylnaphthalene, diethylnaphthalene, etc., paraffins such as ethane, propane, n-butane, isobutane, n-pentane, isopentane, n-hexane, n-heptane, n-octane, n-nonane, n-decane, and branched chain isomers thereof, cycloparaffins such as cyclobutane, cyclopentane, cyclohexane, methylcyclopentane, methylcyclohexane, ethylcyclopentane, olefins such as 1-butene, 2-butene, 1-pentene, 2-pentene, 1-hexene, 2-hexene, 3-hexene, and branched chain derivatives thereof, etc.

The selective oxidation catalysts which are employed in the process of the present invention will comprise a noble metal of Group VIII of the Periodic Table and a metal of Group IVA of the Periodic Table composited on a solid inorganic support, and preferably an inorganic highly porous material possessing a relatively high surface area, that is, a surface area within the range of from about 1 to about 500 m$^2$/g. In addition, if so desired, it is also contemplated within the scope of this invention that the catalyst composite will also contain a metal selected from Groups IA and IIA of the Periodic Table. Of the noble metals of Group VIII of the Periodic Table, platinum, palladium and rhodium comprise the preferred species, said metals being present in the final composite in an amount in the range of from about 0.01% to about 5% by weight. Of the metals of Group IVA of the Periodic Table, germanium, tin and lead comprise the preferred species, these metals also being present in the final catalyst composite in an amount in the range of from about 0.01% to about 5% by weight. The preferred species of metals of Group IA or IIA of the Periodic Table will include potassium, rubidium, cesium, barium, francium, and radium, the alkali metals or alkaline earth metals being present in an amount in the range of from about 0.01% to about 10% by weight of the catalyst composite. The aforesaid metals are composited on a solid inorganic support having the necessary highly porous configuration, some specific examples of these highly porous supports which may be employed will include aluminas such as alpha-alumina, gamma-alumina, eta-alumina, theta-alumina, silica, mixtures of inorganic oxides such as silica-alumina, silica-zirconia, alumina-zirconia-silica, silicon carbide, etc. The selective oxidation catalyst which is utilized in the process of this invention may be prepared in any suitable manner known in the art. For example, one type of preparation will comprise impregnating the solid support which may be in the form of beads, spheres, pellets, etc. with an aqueous solution of a Group VIII metal compound of the Periodic Table. The aqueous solution of the noble metal-containing compound may be prepared from soluble salts of these metals, such as chloroplatinic acid, chloropalladic acid, rhodium chloride, platinum sulfate, palladium sulfate, etc. The solid support is impregnated with the solution for a period of time which is sufficient to allow the deposition of the desired amount of the noble metal on the solid support, that is, an amount sufficient so that the finished catalytic composition will contain from about 0.001% to about 5% by weight of the composite. After recovery of the impregnated solid support, the composite is then dried and calcined at a temperature in the range of from about 500° to about 600° C. or more in an air atmosphere.

The thus formed composite containing a noble metal may then be further impregnated with an aqueous solution of a metal of Group IVA of the Periodic Table. In a similar manner to that hereinbefore described, the amount of soluble salts such as tin chloride, tine bromide, tin sulfate, lead chloride, lead persulfate, germanium chloride, etc. will be present in the solution sufficient so that the finished catalytic composition will contain the desired amount of metals. Again, the impregnation is allowed to proceed for a predetermined period of time following which the composite is recovered, dried and calcined. In the event that it is desired to have a metal of Group IV or IIA of the Periodic Table present in the catalyst composite, the third step of the process is effected in a similar manner by subjecting the composite to an impregnation utilizing an aqueous solution containing the desired metal. Examples of salts of these metals which may be employed will include potassium chloride, potassium bromide, potassium iodide, potassium nitrate, potassium sulfate, potassium acetate, potassium propionate, rubidium chloride, rubidium bromide, rubidium iodide, rubidium nitrate, rubidium sulfate, rubidium acetate, rubidium propionate, cesium chloride, cesium bromide, cesium iodide, cesium nitrate, cesium sulfate, cesium acetate, cesium propionate, calcium chloride, barium chloride, barium bromide, barium iodide, barium nitrate, barium sulfate, barium acetate, barium propionate, etc. After allowing the impregnation to proceed for a period of time sufficient to permit the deposition of the desired amount of metal on the catalyst, the composite is recovered, dried and calcined at a temperature within the range hereinbefore set forth, and recovered.

It is also contemplated that the preparation of the selective oxidation catalyst may be prepared by co-impregnating the noble metal of Group VIII of the Periodic Table, the metal of Group IVA of the Periodic Table, and, if so desired, the metal of Group IA or IIA of the Periodic Table on the solid support. When such a type of preparation is employed, the solid support, such as alumina, is impregnated with an aqueous solution containing salts of the noble metal and the the Group IVA metal along with, if so desired, the alkali metal or alkaline earth metal in a manner similar to that hereinbefore set forth. After allowing the impregnation to proceed for a predetermined period of time, the composite is recovered, dried and calcined at a temperature within the range hereinbefore set forth in an air atmosphere, following which it is recovered for use in the oxidation portion process of the present invention.

Some specific examples of selective oxidation catalytic compositions of matter which may be used in the process of the present invention will include platinum, germanium and potassium composited on alumina, palladium, germanium and potassium composited on alumina, rhodium, germanium and potassium composited on alumina, platinum, tin and potassium composited on alumina, palladium, tin and potassium composited on alumina, rhodium, tin and potassium composited on alumina, platinum, germanium and cesium composited on alumina, palladium, germanium and cesium composited on alumina, rhodium, germanium and cesium composited on alumina, platinum, tin and cesium composited on alumina, palladium, tin and cesium composited on alumina, rhodium, tin and cesium composited on alumina, platinum, germanium and barium composited on alumina, palladium, germanium and barium composited on alumina, rhodium, germanium and barium composited on alumina, platinum, tin and barium composited on alumina, palladium, tin and brium composited on alumina, rhodium, tin and barium composited on alumina, platinum, lead and potassium composited on alumina, palladium, lead and potassium composited on alumina, rhodium, lead and potassium composited on alumina, etc. It is to be understood that the above enumerated catalysts are only representative of the selective oxidation composites which may be used in the process of this invention, and that said invention is not necessarily limited thereto. By utilizing a selective oxidative catalytic composition of matter in a process which involves the dehydrogenation of dehydrogenatable hydrocarbons, it is possible to obtain a process which, in addition to obtaining a desirable and commercially attractive yield of dehydrogenation products, also permits the operation of the process in an economically viable manner due to the catalytic stability of the catalyst under the relatively harsh and stringent operating conditions such as high temperature and high concentration of steam at which the process is operated. This is in contradistinction to prior art types of oxidative catalysts which do not possess the stability of the present catalysts and cannot survive for a long period of time, thus makin the commercial use of such catalysts unattractive due to the necessity of having to replace or regenerate the catalyst after a short inverval of operating time has elapsed. In addition, the catalysts of the present invention also exhibit a definite affinity for the selective oxidation of hydrogen rather than a tendency for the oxidation of the dehydrogenated products.

The following examples are given for purposes of illustrating the process of the present invention utilizing a selective oxidation catalyst in said process. However, it is to be understood that these examples are given merely for purposes of illustration and that the present invention is not necessarily limited thereto.

EXAMPLE I

In this example, an oxidation catalyst was prepared by impregnating 500 cc of 1/16" diameter gamma-alumina beads with an aqueous chloroplatinic acid solution at about 100° C. The alumina was impregnated for a period of 2 hours following which the impregnated alumina was dried and calcined at a temperature of about 540° C. for a period of 2 hours in the presence of a gas consisting of a mixture of air and steam. The impregnated samples was then further impregnated with an aqueous solution of potassium nitrate at about 100° C. for 2 hours following which the sample was recovered, dried and calcined at 540° C. for 2 hours. The impregnated composite which was recovered from the calcination step contained 0.79% by weight of platinum and 2.78% by weight of potassium. In addition, the composite had a surface area of 152 $m^2/g$, a pore volume of 0.41 cc/g, and an ABD of 0.522 g/cc.

The catalyst was loaded into a $\frac{7}{8}$" inner diameter stainless steel tube reactor having a 10" long $\frac{1}{4}$" diameter bore for the catalyst loading. The reactor was heated to an inlet temperature of 600° C. and a feed stream comprising a mixture of ethylbenzene, styrene, steam, hydrogen, oxygen and nitrogen which simulated a product stream at about a 60% ethylbenzene conversion from the second dehydrogenation catalyst bed of a 3-dehydrogenation catalyst bed reactor system having an oxidation catalyst bed positioned between the dehydrogenation catalyst beds, was fed to the reactor. The feed stream was passed over the oxidation catalyst bed at the aforesaid inlet temperature, and a pressure of 0.5 atmospheres at a Liquid Hourly Space Velocity of 100 $hrs^{-1}$. The molar feed ratio of the feed stream of ethylbenzene/styrene/steam/hydrogen/oxygen/nitrogen was 1/1.48/17.9/1.14/0.25/2.21. The conversion of the oxygen was plotted for a period of 250 hours, the results of said run being set forth in Table I below. In this Table, column A is the % conversion of oxygen and column B is the mole % selectivity for oxygen reacting to form carbon dioxide and carbon monoxide.

TABLE I

| Hours on Stream | A | B |
|---|---|---|
| 50 | 65 | 26 |
| 100 | 65 | 23 |
| 150 | 66 | 24 |
| 200 | 63 | 23 |
| 250 | 59 | 21 |

EXAMPLE II

A selective oxidation catalyst was prepared in a manner similar to that set forth in Example I above. In this example, 4630 cc of 1/16" diameter beads of a tin oxide-gamma-alumina cogel were impregnated with an aqueous solution of chloroplatinic acid at about 100° C. The tin oxide-alumina beads were impregnated for a period of 10 hours following which the impregnated beads were recovered, dried and calcined at a temperature of about 320° C. for a period of 30 minutes and at 565° C. for 1 hour, said calcination being effected in the presence of a gas consisting of a mixture of air and steam. The sample was then impregnated with an aqueous solution of potassium nitrate at about 100° C. for a period of 10 hours, following which the impregnated beads were recovered, dried and calcined at a temperature of about 320° C. for 30 minutes, and at 565° C. for 1 hour. The catalyst was reduced with hydrogen at about 475° C. for 4 hours. The impregnated composite which was recovered from the calcination step contained 0.75% by weight of platinum, 0.5% by weight of tin, and 2.44% by weight of potassium. The composite had a surface area of 182 $m^2/g$, a pore volume of 0.60 cc/g, and an ABD of 5.90 g/cc.

The catalyst was loaded into a $\frac{7}{8}$" inner diameter stainless steel tube reactor having a 10" long $\frac{1}{4}$" diameter bore for the catalyst loading. A feed stream comprising a mixture of ethylbenzene, styrene, steam, hydrogen, oxygen and nitrogen in a molar feed ratio similar to that set forth in Example I above, and which simulated a product stream from a dehydrogenation step was passed over the selective oxidation bed in an inlet temperature of 600° C., a pressure of 0.5 atmospheres at a Liquid Hourly Space Velocity of 100 $hrs^{-1}$. As in Example I above, the conversion of the oxygen was plotted for a period of 250 hours. The results of this run are set forth in Table II below in which column A refers to the % conversion of oxygen and column B refers to the mole % selectivity for oxygen reacting to carbon dioxide and carbon monoxide.

TABLE II

| Hours on Stream | A | B |
|---|---|---|
| 50 | 62 | 10 |
| 100 | 61 | 11 |
| 150 | 59 | 8 |
| 200 | 59 | 8 |
| 250 | 59 | 9 |

It is apparent from a comparison of the above tables that the selective oxidation catalyst which comprised a noble metal of Group VIII of the Periodic Table, namely platinum, a metal of Group IVA of the Periodic Table, tin and a metal of Group IA of the Periodic Table, potassium, exhibited a much lower selectivity of oxygen which reacted to form carbon dioxide and carbon monoxide than did the catalyst which contained only platinum and potassium. This is indicative of an improved selectivity to a hydrogen combustion with a concomitant low selectivity to a reaction with the hydrocarbons present, thus permitting or resulting in a greater yield of the desired dehydrogenated hydrocarbon and unconverted hydrocarbons which may be recycled back for further dehydrogenation.

EXAMPLE III

To illustrate further the efficiency of the process of the present invention, a comparison is made between the instant process and the process described in U.S. Pat. No. 3,670,044. It is noted from Example II above that for 100 hours of operation there has been a 61% conversion of the oxygen with an 11% selectivity for the oxygen reacting with ethylbenzene and styrene to form carbon dioxide. Using a feed of ethylbenzene/styrene/oxygen which had 1 mole of ethylbenzene, 1.48 moles of styrene, and 0.25 mole of oxygen, the amount of carbon dioxide which was produced equaled 0.0168 mole. Therefore, by means of oxidation, 8 moles of carbon dioxide are produced from 1 mole of ethylbenzene or styrene and the amount of ethylbenzene plus styrene which is converted into carbon dioxide is 0.0021 mole. The loss of feed to carbon dioxide due to the selective oxidation of hydrogen in the process of the present invention equals 0.085%.

In contradistinction to this, the patent shows, as exemplified by Example III therein, that there was a 49% conversion of n-butane with a 1% selectivity to carbon dioxide. Therefore, 0.49% of the n-butane which was fed into the system was converted into carbon dioxide. A comparison of the two figures shows therefore that the loss of feed to carbon dioxide in the patent was greater than the loss of feed to carbon dioxide in the present invention. This difference is due to the use of a selective oxidation catalyst of the type hereinbefore described.

EXAMPLE IV

A comparison of the process of the present invention in which the selective oxidation of hydrogen is utilized to reheat the dehydrogenation step of the process with a process in which the dehydrogenation temperature is attained by heating with steam results in not only an advantage in the yield of the desired product, but also an advantage in the utility or energy requirements. In a conventional process in which a dehydrogenatable hydrocarbon such as ethylbenzene is treated with a dehydrogenation catalyst in the presence of steam, the results show a 70% conversion of the ethylbenzene while utilizing 23 moles of superheated steam to produce 1 mole of styrene.

EXAMPLE V

In a like manner, other selective oxidation catalysts comprising platinum or rhodium along with germanium or lead and, if so desired, cesium, strontium or barium, composited on other inorganic supports such as silica, nonacidic silica-alumina, or silicon carbide which possesses physical characteristics of surface area, pore volume, and ABD's to that of alumina may also show similar results when used as selective oxidation catalysts in a dehydrogenation reaction involving the treatment of a dehydrogenatable hydrocarbon with a dehydrogenation catalyst.

I claim as my invention:

1. A process for the dehydrogenation of a dehydrogenatable hydrocarbon with separate and intermediate selective oxidation of hydrogen which compises:
   (a) contacting said hydrocarbon with a dehydrogenation catalyst comprising an alkaline metal-promoted iron compound in a first reaction-dehydrogenation zone in the presence of steam to produce a first reaction-dehydrogenation zone effluent stream comprising a mixture of uncoverted hydrocarbons, dehydrogenated hydrocarbons, hydrogen and steam;
   (b) removing said first-reaction dehydrogenation zone effluent from said first reaction-dehydrogenation zone;
   (c) passing said removed first-reaction dehydrogenation zone effluent of step (b) to a second-reaction oxidation zone, which is separate and discrete from said-reaction dehydrogenation zone;
   (d) contacting said first-reaction dehydrogenation zone effluent in said second-reaction oxidation zone with an oxygen-containing gas to selectively oxidize said hydrogen within said first-reaction dehydrogenation zone effluent to the substantial exclusion of oxidation of said unconverted and dehydrogenated hydrocarbons in the presence of an oxidation catalyst consisting essentially of about 0.01 to about 5 wt% of a Group VIII noble metal, about 0.01 to about 5wt% of a Group IVA metal, and from about 0.01 to about 10% by weight of a metal of Group IA or IIA composited on a highly porous alumina support at oxidation conditions, wherein said exothermic selective oxidation of said hydrogen provides additional heat and thereby raises the temperature of said unconverted and dehydrogenated hydrocarbons;
   (e) withdrawing said unconverted and dehydrogenated hydrocarbons from said second-reaction oxidation zone having an increased temperature with respect to the temperature of said first-reaction dehydrogenation effluent zone;
   (f) passing said removed second reaction-oxidation zone product stream of step (e) to a third-reaction dehydrogenation zone, containing a dehydrogenation catalyst comprising an alkaline metal promoted iron compound at dehydrogenation conditions to produce dehydrogenated hydrocarbons; and
   (g) withdrawing and recovering said dehydrogenated hydrocarbons.

2. The process as set forth in claim 1 in which said alkaline metal of said dehydrogenation catalyst is selected from the group consisting of Group IA and IIA of the Periodic Table.

3. The process as set forth in claim 1 in which said dehydrogenation catalyst contains an oxide or sulfide of a metal selected from the group consisting of Groups IVB, VB and VIB of the Periodic Table.

4. The process as set forth in claim 1 in which said dehydrogenation and oxidation conditions include a temperature in the range of from about 500° to about 700° C. and a pressure in the range of from about 0.1 to about 10 atmospheres.

5. The process as set forth in claim 1 in which said oxygen-containing gas is oxygen.

6. The process as set forth in claim 1 in which said oxygen-containing gas is air.

7. The process as set forth in claim 1 in which said oxidation catalyst also consists essentially of a metal of Group IA or IIA of the Periodic Table.

8. The process as set forth in claim 1 in which the noble metal of Group VIII of the Periodic Table is selected from the group consisting of platinum, palladium and rhodium.

9. The process as set forth in claim 1 in which the metal of Group IVA of the Periodic Table is selected from the group consisting of germainum, tin and lead.

10. The process as set forth in claim 1 in which the metal of Group IA or IIA of the Periodic Table is selected from the group consisting of potassium, rubidium, cesium, strontium and barium.

11. The process as set forth in claim 1 in which the dehydrogenatable hydrocarbon is ethylbenzene and said dehydrogenated hydrocarbon is styrene.

* * * * *